United States Patent
Acharya et al.

(10) Patent No.: US 7,521,174 B2
(45) Date of Patent: Apr. 21, 2009

(54) UNIVERSAL RED BLOOD CELLS, METHODS OF PREPARING SAME, AND USES THEREOF

(75) Inventors: Seetharama A. Acharya, Cresskill, NJ (US); Parimala Nacharaju, Staten Island, NY (US); Belur N. Manjula, Cresskill, NJ (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 391 days.

(21) Appl. No.: 11/004,052

(22) Filed: Dec. 3, 2004

(65) Prior Publication Data

US 2005/0201988 A1 Sep. 15, 2005

Related U.S. Application Data

(60) Provisional application No. 60/527,577, filed on Dec. 5, 2003.

(51) Int. Cl.
*A01N 1/02* (2006.01)
(52) U.S. Cl. .......................................................... 435/2
(58) Field of Classification Search ....................... None
See application file for complete search history.

(56) References Cited

U.S. PATENT DOCUMENTS

| | | | |
|---|---|---|---|
| 4,412,989 A | 11/1983 | Iwashita et al. |
| 5,234,903 A | 8/1993 | Nho et al. |
| 5,386,014 A | 1/1995 | Nho et al. |
| 5,585,484 A | 12/1996 | Acharya et al. |
| 5,750,725 A | 5/1998 | Acharya et al. |
| 5,908,624 A | 6/1999 | Scott et al. |
| 6,017,943 A | 1/2000 | Acharya et al. |
| 6,129,912 A | 10/2000 | Hortin et al. |
| 6,312,685 B1 | 11/2001 | Fisher et al. |
| 6,737,524 B2 | 5/2004 | Smith |
| 7,019,117 B2 | 3/2006 | Acharya et al. |
| 7,144,989 B2 | 12/2006 | Acharya et al. |
| 7,169,900 B2 | 1/2007 | Acharya et al. |
| 2004/0002443 A1 | 1/2004 | Acharya et al. |
| 2004/0127697 A1 | 7/2004 | Smith |
| 2004/0147736 A1 | 7/2004 | Smith |
| 2006/0135753 A1 | 6/2006 | Acharya et al. |

FOREIGN PATENT DOCUMENTS

| WO | 2004/049914 | * | 6/2004 |
|---|---|---|---|
| WO | 2004/050029 | * | 6/2004 |
| WO | WO 2006/135740 A1 | | 12/2006 |
| WO | WO 2007/050121 A2 | | 5/2007 |
| WO | WO 2007/058678 A2 | | 5/2007 |

OTHER PUBLICATIONS

Laysan Bio., Inc. Catalog, www.laysanbio.com, accessed Jun. 27, 2007.*
Grant & Hackh's Chemical Dictionary, Fifth Edition, p. 461, definition of polyethylene glycol, McGraw-Hill Book Co. 1987.*
Roberts MJ, et al., entitled "Chemistry for peptide and protein PEGylation," Adv Drug Deliv Rev. Jun. 17, 2002;54(4):459-76.
Sabolovic D., et al., entitled "Covalent binding of polyethylene glycol to the surface of red blood cells as detected and followed up by cell electrophoresis and rheological methods," Electrophoresis Jan. 2000;21(2):301-6.
Bradley AJ, et al., entitled "Interactions of IgM ABO antibodies and complement with methoxy-PEG-modified human RBCs," Transfusion. Oct. 2001;41(10):1225-33.
Bradley AJ, et al., entitled "Biophysical consequences of linker chemistry and polymer size on stealth erythrocytes: size does matter," Biochim Biophys Acta. Apr. 12, 2002:1561(2): 147-58.
Jeong ST, et al., entitled "Decreased agglutinability of methoxypolyethylene glycol attached red blood cells: significance as a blood substitute," Artif Cells Blood Substit Immobil Biotechnol. Sep. 1996;24(5):503-511.
Blackall, DP., et al., entitled "Polyethylene glycol-coated red blood cells fail to bind glycophorin A-specific antibodies and are impervious to invasion by the *Plasmodium falciparum* malaria parasite," Blood, 15, Jan. 2001, vol. 97, No. 2, pp. 551-556.
Scott MD, et al., entitled "Chemical camouflage of antigenic determinants: Stealth erythrocytes," Proc. Natl. Acad. Sci., vol. 94, pp. 7566-7571, Jul. 1997.

\* cited by examiner

*Primary Examiner*—Sandra E. Saucier
(74) *Attorney, Agent, or Firm*—Amster, Rothstein & Ebenstein LLP

(57) ABSTRACT

The present invention is directed to pegylated red blood cells comprising a polyethylene glycol (PEG) attached to a thiolated amino group on a membrane protein, and to compositions comprising the pegylated red blood cells. The invention also provides methods of preparing pegylated red blood cells comprising reacting red blood cells with a compound that produces a thiolated amino group on a red blood cell membrane protein, and reacting the thiolated red blood cell with a PEG. The invention further provides methods of treatment using pegylated red blood cells.

21 Claims, 7 Drawing Sheets

UNIVERSAL RED BLOOD CELLS, METHODS OF PREPARING SAME, AND USES THEREOF

CROSS-REFERENCE TO RELATED APPLICATION

This application claims the benefit of U.S. Provisional Patent Application No. 60/527,577, filed on Dec. 5, 2003, the contents of which are hereby incorporated by reference into the subject application.

STATEMENT OF GOVERNMENT SUPPORT

This invention was made with United States government support under grant number HL-71064 from the National Institutes of Health. Accordingly, the United States government has certain rights in this invention.

BACKGROUND OF THE INVENTION

Blood transfusion has been a major option for the treatment of diseases such as sickle cell anemia and thalassemia. Surgery and trauma conditions also often require blood transfusion. In most of the cases a match between patient and donor blood is made by testing for major group antigens ABO and RhD. However, patients receiving blood transfusion repeatedly develop alloimmunization against non-ABO/RhD antigens (e.g., Castro et al., 2002). Eventually, it becomes very difficult to find a perfect donor for such patients. This problem is more prominent for sickle cell patients who are usually of African origin while the donors are usually whites (e.g., Issitt, 1994). The difference in the Rh antigens between these two communities is a major concern about allosensitization in sickle cell patients.

Attempts have been made to generate universal erythrocytes to overcome difficulties such as those mentioned above. Universal erythrocytes are needed especially for trauma conditions where there is no time to perform tests for blood group matching. Enzymatic digestion has been used to remove antigen specific carbohydrates from the membrane of red blood cells (RBCs) (Goldstein et al., 1982). B group RBCs have been converted to O group RBCs by enzymatic cleavage of the B group specific antigen, galactose. These RBCs have been successfully transfused into O group individuals (Lenny et al., 1994, 1995). However, this strategy requires the use of different enzymes to remove different types of antigens. Moreover, this protocol cannot be used for protein antigens such as the Rh system since these proteins are closely associated with the cell membrane (Avent and Reid, 2000).

Masking antigens by attaching bulky polymer chains to the surface of RBCs has been used as another approach to develop universal RBCs. Functionalized polyethylene glycol (PEG) chains have been used to modify RBC membrane proteins (Bradley et al., 2002; Jeong and Byun, 1996; Scott et al., 1997; U.S. Pat. No. 6,312,685). These PEG chains by being hydrophilic become heavily hydrated and can cover a large surface area of the RBC membrane and thus can prevent the accessibility of the blood group antigens to antibodies. PEG-cyanuric chloride is the most common reagent used for pegylation of erythrocytes (Blackall et al., 2001; Bradley et al., 2001, 2002; Jeong and Byun, 1996; Sabolovic et al., 2000; Scott et al., 1997; U.S. Pat. No. 6,312,685). This functionalized PEG reagent modifies mostly amino groups on proteins (Roberts et al., 2002). Pegylation of RBCs with PEG-5000 activated with cyanuric chloride has been reported to mask Rh antigens to a reasonable extent. In contrast, A or B antigens were only partially masked by this procedure (Bradley et al., 2001; Jeong and Byun, 1996; Scott et al., 1997; U.S. Pat. No. 6,312,685). Masking of the A and B antigens of RBCs is critical for developing universal red blood cells.

SUMMARY OF THE INVENTION

The present invention provides a pegylated red blood cell comprising polyethylene glycol (PEG) attached to thiolated amino groups on a membrane protein of the red blood cell, wherein at least one amino acid of the membrane protein is thiolated using a chemical compound prior to attaching the polyethylene glycol (PEG). A, B and Rh antigens are masked on pegylated red bloods cells of the present invention.

The present invention also provides a method of treating a subject which comprises administering to the subject a pegylated red blood cell comprising a polyethylene glycol (PEG) attached to a thiolated amino group on a membrane protein of the red blood cell.

The present invention further comprises a method of preparing a pegylated red blood cell, comprising (a) reacting a red blood cell with a chemical compound that produces a thiolated amino group on a membrane protein of the red blood cell, and (b) reacting the thiolated red blood cell with a polyethylene glycol (PEG) to provide a pegylated red blood cell.

Additional objects of the invention will be apparent from the description which follows.

DETAILED DESCRIPTION OF THE INVENTION

The present invention is directed to a pegylated red blood cell comprising a polyethylene glycol (PEG) attached to a thiolated amino group on a membrane protein of the red blood cell, wherein at least one amino acid of the membrane protein is thiolated using a chemical compound prior to attaching the polyethylene glycol (PEG).

Figure 1:
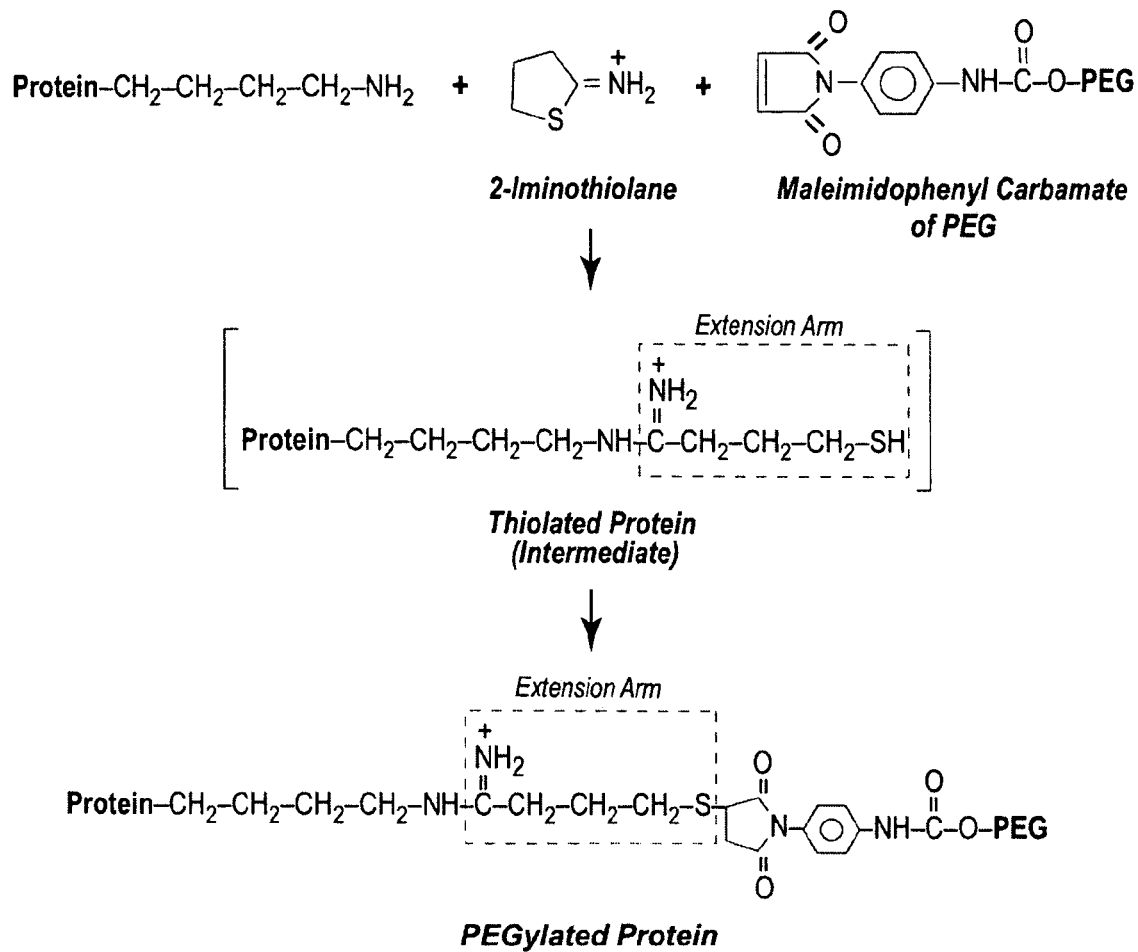
FIG. 1. Schematic representation of the 2-iminothiolane-thiolation mediated PEGylation of erythrocyte membrane proteins. ε-amino groups of lysine residues of membrane proteins are modified by 2-iminothiolane generating thiol groups at the end of an extension arm. These thiol groups subsequently are modified by PEG, e.g., Mal-Phe-PEG, forming PEGylated proteins.

As used herein, "pegylation" means linking to PEG, and a "pegylated" red blood cell (RBC) is a RBC attached to PEG. Preferably, the polyethylene glycol (PEG) is a maleimide polyethylene glycol (PEG) and/or a succinimidyl-propionate-activated (SPA) PEG. Preferably, the PEG is attached to the amino group via a linker and/or an extension arm. As used herein, an "extension arm" refers to the carbon chain—thiol group that is attached to the amino group of the RBC during the thiolation process, for example, as shown schematically in FIG. 1 for thiolation using 2-iminothiolane. The extension arm places the thiol group away from the surface of the RBC, thereby enhancing the accessibility of the thiol group to bulky PEG reagents.

The linker or extension arm can comprise an alkyl, aryl and/or heteroaryl group. For example, the alkyl group can be a propyl group, and the aryl group can be a phenyl group. The linker or extension arm can comprise a δ-mercapto butyrimidyl chain or a γ-mercapto propylamide chain.

The chemical compound used for thiolation can be, for example, iminothiolane or preferably dithio sulfo succinimidyl propinate (DTSSP).

Preferably, the pegylated red blood cell comprises a PEG with a molecular weight of 200-40,000 daltons. PEGs of various molecular weights, conjugated to various groups, can be obtained commercially, for example from Nektar Therapeutics, Huntsville, Ala. More preferably, the pegylated red blood cell comprises a PEG with a molecular weight of 2000-5000 daltons, and a PEG with a molecular weight of 10,000-35,000 daltons. Most preferably, the pegylated red blood cell comprises a PEG-5000 and a PEG-20,000. The PEGs can be, for example, maleimide PEGs and/or SPA-PEGs. A preferred embodiment comprises a maleimide PEG-5000 and a SPA-PEG-20,000.

The maleimide PEG can be, for example, a maleimide phenyl PEG or a maleimide PEG comprising an alkyl linker. Preferably, the maleimide phenyl PEG is a maleimide phenyl PEG-20,000, a maleimide phenyl PEG-10,000, and/or a maleimide phenyl PEG-5,000. Preferably, the maleimide PEG comprising an alkyl linker has a linker comprising a propyl group.

Preferably, the pegylated sites on the pegylated red blood cell comprise the Band III protein that carries an A and/or B blood type antigen. Preferably, the thiolated amino group is an ε-amino group of a lysine residue. Preferably, the PEG-chains are conjugated to the red blood cell in a "brush" configuration as opposed to a "mushroom" configuration.

Preferably, agglutination of pegylated red blood cells is inhibited or prevented in the presence of blood type specific antibodies, including anti-A, an anti-B, and/or an anti-Rh antibody. Rh antigens include subtypes C, D, E, c and e. In one embodiment, the PEG is a maleimide phenyl PEG-5,000 or a maleimide phenyl PEG-10,000, and the pegylated red blood cells do not agglutinate in the presence of an anti-Rh(D) antibody. Preferably, the pegylated red blood cell comprises a maleimide PEG with a molecular weight of 2000-5000 daltons, more preferably a maleimide PEG-5000, and a PEG with a molecular weight of 10,000-35,000 daltons, more preferably a PEG-20,000, and agglutination of the pegylated red blood cells is inhibited or prevented in the presence of an anti-A antibody, anti-B antibody and/or an anti-Rh antibody, preferably, an anti-Rh(D) antibody.

Preferably, pegylation does not alter the surface charge of the thiolated amino group. Preferably, the pegylated red blood cell has a storage life that is as long or longer than a non-pegylated red blood cell under identical storage conditions. Preferably, pegylation does not diminish the ability of the red blood cell to transport oxygen.

Preferably, pegylation does not alter the oxygen affinity of the red blood cell by more than 20% or by more than 15%.

The invention also provides a method of preparing a pegylated red blood cell, comprising (a) reacting a red blood cell with a chemical compound that produces a thiolated amino group on a membrane protein of the red blood cell, and (b) reacting the thiolated red blood cell with a polyethylene glycol (PEG) to provide a pegylated red blood cell.

Preferably, the PEG has a molecular weight of 200-40,000 daltons. The method can comprise first reacting the red blood cell with a PEG with a molecular weight of 2000-5000 daltons in the presence of a compound that produces a thiolated amino group, and then reacting the red blood cell with a PEG with a molecular weight of 10,000-35,000 daltons in the presence of a compound that produces a thiolated amino group. More preferably, the method comprises first reacting the red blood cell with a PEG-5000 in the presence of a compound that produces a thiolated amino group, and then reacting the red blood cell with a PEG-20,000 in the presence of a compound that produces a thiolated amino group.

The method can also comprise first reacting the red blood cell with a PEG with a molecular weight of 2000-5000 daltons in the presence of a compound that produces a thiolated amino group, and then reacting the red blood cell with a PEG with a molecular weight of 10,000-35,000 daltons in the absence of a compound that produces a thiolated amino group. More preferably, the method comprises first reacting the red blood cell with a PEG-5000 in the presence of a compound that produces a thiolated amino group, and then reacting the red blood cell with a PEG-20,000 in the absence of a compound that produces a thiolated amino group.

The PEG can be, for example, a maleimide PEG and/or an SPA-PEG, for example a maleimide PEG-5000 and a SPA-PEG-20,000. The maleimide PEG can be, for example, a maleimide phenyl PEG, for example a maleimide phenyl PEG-20,000, a maleimide phenyl PEG-10,000, and/or a maleimide phenyl PEG-5,000. The maleimide PEG can comprise an alkyl linker, for example a propyl group.

Preferably, the PEG is attached to the amino group via a linker and/or an extension arm. The linker or extension arm can comprise an alkyl, aryl and/or heteroaryl group. For example, the alkyl group can be a propyl group, and the aryl group can be a phenyl group. The linker or extension arm can comprise a δ-mercapto butyrimidyl chain or a γ-mercapto propylamide chain.

The chemical compound that is used to produce the thiolated amino group can be iminothiolane or preferably dithio sulfo succinimidyl propinate (DTSSP).

Preferably, the pegylation occurs at sites that comprise the Band III protein that carries an A and/or B blood type antigen. Preferably, the amino group that is thiolated is an ε-amino group of a lysine residue. Preferably, pegylation does not alter the oxygen affinity of the red blood cell by more than 15% or 20%.

The method can be carried out at a temperature between about room temperature and about 4° C. The method can be carried out at a pH of about 7.4-9.2. The method can be carried out using a duration of about 2 hours. In a preferred embodiment, varying the concentration of the chemical compound that is used to produce the thiolated amino groups affects the number of pegylated sites on the red blood cell.

The invention further provides a method of preparing a pegylated red blood cell, comprising (a) reacting a red blood cell with a SPA-polyethylene glycol (PEG) with a molecular weight of 2000-5000 daltons; and then (b) reacting the pegylated red blood cell with a SPA-polyethylene glycol (PEG) with a molecular weight of 10,000-35,000 daltons. Preferably, the SPA-PEG in step (a) is a SPA-PEG-5,000. Preferably, the SPA-PEG in step (b) is a SPA-PEG-20,000. Preferably, pegylation does not alter the oxygen affinity of the red blood cell.

The invention provides a pegylated red blood cell produced by any of the methods disclosed herein.

Preferably, agglutination of any of the pegylated red blood cells described herein is inhibited or prevented in the presence of blood type specific antibodies. The blood type specific antibody can be an anti-A, an anti-B, and/or an anti-Rh antibody. Rh antigens include subtypes C, D, E, c and e.

Preferably, pegylation does not alter the surface charge of the thiolated amino group. Preferably, pegylation does not alter the storage life of the red blood cell. Preferably, pegylation does not diminish the ability of the red blood cell to transport oxygen.

The invention also provides a composition comprising any of the pegylated red blood cells disclosed herein, and a pharmaceutically acceptable carrier. Pharmaceutically acceptable carriers include, but are not limited to, additive solution-3 (AS-3), saline, phosphate buffered saline, Ringer's solution, lactated Ringer's solution, Locke-Ringer's solution, Kreb's Ringer's solution, Hartmann's balanced saline solution, and/or heparinized sodium citrate acid dextrose solution. The pharmaceutical compositions also may comprise known plasma substitutes and plasma expanders. The pharmaceutical compositions of the present invention may be used as blood substitutes, and the like, and may be administered by conventional means including but not limited to transfusion and injection.

The invention further provides a method of treating a subject which comprises administering to the subject any of the pegylated red blood cells disclosed herein or any pegylated red blood cell prepared by any of the methods disclosed herein. Prior to treatment, the subject may have a reduced red blood cell count and/or a reduced blood volume. The subject may have a disease characterized by vaso-occlusion and/or impaired blood flow. Such diseases include, but are not limited to, sickle cell disease, myocardial infarction and/or shock.

The present invention is illustrated in the following Experimental Details section, which is set forth to aid in the understanding of the invention, and should not be construed to limit in any way the scope of the invention as defined in the claims that follow thereafter.

EXPERIMENTAL DETAILS

I. Overview

PEGylation of thiolated amino groups of erythrocyte membrane proteins was used to mask A, B and Rh antigens. Dithiosulfosuccinimidyl propionate (DTSSP) and iminothiolane (IT) were used to generate thiol groups on lysine residues, which were then modified by PEG. While generating thiol groups on lysine residues, DTSSP and IT add a carbon chain between the nitrogen atom of the amino group and the sulfur atom of the new thiol group introduced onto the protein. This is illustrated schematically for IT in FIG. 1. The presence of the carbon chain in this carbon chain—thiol "extension arm" is believed to enhance the accessibility of these thiols to the bulky PEG reagent. Thus, a higher number of PEG chains can be attached to the surface of RBCs using this chemistry than using a PEG reagent that is targeted directly to the amino groups.

II. Materials and Methods

Mal-Phe-PEG reagents were synthesized as described in Manjula et al., 2003. Cyanuric chloride-PEG-5000 (CnCl-PEG-5000) and rabbit anti-mouse IgG-FITC were obtained from Sigma Chemical CO., St. Louis, Mo. Two-iminothiolane was purchased from Pierce, Rockford, Ill. Blood typing monoclonal, IgG type antisera were purchased from ImmucorGamma, Norcross, Ga. Blood samples were collected from healthy volunteers in heparin. The red blood cells were washed at least three times with incubation buffer, pH 7.4 (50 mM sodium phosphate, 122 mM dextrose, 2 mM adenine, 41 mM mannitol and 154 mM sodium chloride) by centrifugation at 3000 rpm.

PEGylation of RBCs: Thiolation of RBCs was carried out using two different procedures. In one procedure, RBCs of type A1 Rh(D)+, B Rh(D)+ and O Rh(D)+ were PEGylated using Mal-Phe-PEG in the presence of two-iminothiolane (IT). The procedure is illustrated schematically in FIG. 1. Due to the presence of the "extension arm" introduced by the thiolation procedure, the new thiol site for attachment of PEG is approximately 8 Å away from the original amino group. Mal-Phe-PEG reagents carrying different length of PEG chains, PEG-5000, PEG-10000 and PEG-20000, were used for PEGylation. Typically, 5% RBCs were incubated with 10 mM Mal-Phe-PEG in the absence or presence of 20 mM IT in incubation buffer, pH 7.4, for 2 hours at room temperature.

In a second thiolation procedure, A Rh(D)+ RBCs (5%) were incubated with 5 mM 3,3'-dithiobis(sulfosuccinimidyl propionate) (DTSSP) at room temperature for 1 hour in incubation buffer (50 mM sodium phosphate, 105 mM sodium chloride, pH 7.4). After washing off the excess reagent the cells were re-incubated with 20 mM Tris(2-carboxyethyl) phosphine (TCEP) for 30 min in the same buffer at room temperature. Again the cells were washed to remove excess TCEP and incubated with 15 mM Mal-Phe-PEG-5K for 2 hours at room temperature. Finally the PEGylated cells were washed with the same buffer. A second step DTSSP mediated PEGylation of RBCs was also carried out in the same way except that 10 mM Mal-Phe-PEG-20K was used.

PEGylation of RBCs with SPA-PEG-5K: Attachment of PEG chains to amino groups of RBCs was carried out using succinimidyl-propionate-activated (SPA) methoxy polyethylene glycol (P5K-SPA, Nektar Therapeutics, Huntsville, Ala.). A Rh(D)+ RBCs (5%) were reacted with 10 mM SPA-PEG-5K for 2 hours at room temperature in the incubation buffer and washed with the same buffer. A second step PEGylation was carried out with 10 mM SPA-PEG-20K.

PEGylation of RBCs with cyanuric chloride-PEG-5K: PEGylation of RBCs with cyanuric chloride-PEG-5000 was carried out as described previously (Bradley et al., 2002; Lenny et al., 1994) with some modifications. 5% RBCs were incubated with 5 mM CnCl-PEG-5000 in 50 mM sodium phosphate, pH 9.2, for 1 hour at room temperature.

After removing the excess reagents by washing with the incubation buffer, RBCs were tested for blockage of the blood type antigens by PEGylation by the standard blood typing test using antibodies against the respective antigens. The agglutination was evaluated at the macroscopic level using an agglutination viewer (Beckton Dickinson, San Jose, Calif.). Samples that gave negative results for agglutination at the macroscopic level were examined under a light microscope (Nikon Eclipse E400, Morrell Instrument CO. Inc., Melville, N.Y.) for further confirmation. Images were collected at 10×0.25 lens.

Flow cytometry of PEGylated cells: RBCs were prepared for flow cytometry as described by de Isla et al. (2003). Type A RhD+ RBCs were first titrated with monoclonal anti-A and anti-D antibodies at different antibody dilutions to determine the highest antibody concentrations to label the cells with rabbit anti-mouse-IgG-FITC without agglutination at the microscopic level. Rabbit normal serum was used to block non-specific binding of rabbit anti-mouse-IgG-FITC. After choosing optimal dilutions for the antibodies, control RBCs and PEGylated RBCs were prepared for flow cytometry.

The labeled RBCs and PEGylated RBCs were analyzed on a flow cytometer (FACScan, Becton Dickinson, San Jose, Calif.) using Cell Quest software. Unlabeled RBCs were used to determine the gate for non-agglutinated cells on the basis of their forward and side scatter on logarithmic scales. These cells served as control to set up negative fluorescence signal. The background fluorescence was determined with the cells that were incubated with anti-mouse-IgG-FITC alone without prior incubation with primary antibodies. A total of 20,000 events were collected for each sample. The background fluorescence was subtracted from the fluorescence of each sample in the data presented.

Oxygen affinity studies: The oxygen affinity of PEGylated RBCs was determined in incubation buffer using Hem-O-Scan at 37° C.

III. Results

Masking of the RhD antigens of RBCs from the cognate antibodies by thiolation mediated PEGylation using Mal-Phe-PEG-5000. Modification of RBCs (A RhD+) by Mal-Phe-PEG-5000 alone could not mask either the A or D antigens, significantly (Table 1). Apparently, the surface of the erythrocyte membrane does not carry enough of intrinsic thiol groups (from Cysteine residues of membrane proteins) to provide the desired level of surface coverage with PEG chains that could mask the antigenic determinants of the cell from the respective antibodies. On the other hand, incubation of RBCs with the same maleimide PEG reagent in the presence of IT inhibited the interaction of the PEGylated RBCs with anti-D as reflected by the complete inhibition of the agglutination of these RBCs by anti-D antibody. These results indicate that IT has introduced new thiol groups onto RBCs and accordingly PEGylation with Mal-Phe-PEG-5000 added more PEG chains to the surface of RBCs that efficiently blocked D antigen from their antibodies. However, this PEGylation in the presence of IT did not mask A antigen to any considerable extent (Table 1).

RBCs of type B Rh(D)+ and O Rh(D)+ were also modified with Mal-Phe-PEG-5000 in the presence of IT. Just as with RBCs of type A Rh(D)+, these PEGylated cells also did not agglutinate in the presence of anti-D antibodies (Table 1). Thus enough protection could be achieved against the RhD antigen of RBCs by thiolation mediated PEGylation of RBCs using Mal-Phe-PEG-5000. However, like the A antigen, the B antigen in B Rh(D)+ RBCs was also not masked by this PEGylation as reflected by the unaltered agglutination of these RBCs with anti-B antibody.

RBCs carrying RhCE antigens homozygous or heterozygous for C and c as well as E and e were also PEGylated with Mal-Phe-PEG-5000 in the presence of IT. The agglutination of these cells in the presence of anti-C, anti-c, anti-E and anti-e antibodies was completely inhibited, demonstrating proper masking of all these antigens by the PEGylation (Table 2). Therefore, PEGylation of RBCs with Mal-Phe-PEG-5000 in the presence of IT camouflages the clinically important antigens of the Rh system.

Influence of the molecular size (length) of PEG-chains on masking of the A and B antigens of RBCs. Although PEGylation of type A Rh(D)+ and B Rh(D)+ RBCs with Mal-Phe-PEG-5000 in the presence of IT inhibited the agglutination of RBCs with antibodies against Rh antigens, these RBCs did not exhibit significant reduction in agglutination by anti-A and anti-B antibodies, respectively. Unlike Rh system antigens that are multipass-transmembrane proteins, the ABO system antigens are carbohydrate dependent. These polysaccharides are of variable length and are attached to proteins and lipids of the RBC membrane. Thus, these antigens are extended more into the solvent than Rh antigens. Therefore, Mal-Phe-PEG reagents with longer PEG chains may be needed to mask these antigens of RBCs effectively. Accordingly, type A Rh(D)+ RBCs were PEGylated with PEG reagents of longer chain length, Mal-Phe-PEG-10000 and Mal-Phe-PEG-20000 in the presence of IT. As mentioned above, RBCs PEGylated using Mal-Phe-PEG 5000 did not exhibit any difference in agglutination with anti-A antibody as compared to the control cells. In contrast, PEGylation by Mal-Phe-PEG-10000 reduced the agglutination of RBCs with anti-A antibody considerably (Table 3). Mal-Phe-PEG-20000 further reduced the agglutination of RBCs with this antibody. Nonetheless, the agglutination with anti-A antibody was not inhibited completely by PEGylation of RBCs with any of these PEG chains.

The RBCs PEGylated with longer chain PEG reagents were also tested for agglutination with anti-D antibody to map the influence of the molecular size of PEG in masking the RhD antigen. Like Mal-Phe-PEG-5000, PEG-10000 also inhibited the agglutination of RBCs by anti-D antibody (Table 3). However, PEG-20000 did not block the agglutination of RBCs by anti-D antibody as much as the other two shorter chain PEG reagents. Thus shorter PEG chain lengths (5000 and 10000) appear to be more suited for masking the protein antigen RhD.

PEGylation of RBCs with a mixture of maleimide PEG reagents for masking of A and B antigens. Mixtures of PEG reagents have been tested for PEGylation of RBCs to mask AB antigens. A Rh(D)+ RBCs incubated with a mixture (1:1) of Mal-Phe-PEG-5000 and Mal-Phe-PEG-10000 in the presence of iminothiolane yielded results similar to that obtained with Mal-Phe-PEG-5000 alone (Table 3). The presence of Mal-Phe-PEG-10000 in the reaction mixture did not make any significant difference. The results obtained with an equimolar mixture of Mal-Phe-PEG-5000 and Mal-Phe-PEG-20000 were comparable to the results obtained with Mal-Phe-PEG-20000 alone. A mixture of all the three PEG reagents, Mal-Phe-PEG-5000, Mal-Phe-PEG-10000 and Mal-Phe-PEG-20000 also could not mask A antigen from anti-A antibody sufficiently.

Thus, type A Rh(D)+ RBCs PEGylated with Mal-Phe-PEG-20000 alone or with a mixture of Mal-Phe-PEG-5000 and Mal-Phe-PEG-20000 exhibited the least agglutination with anti-A antibody. However, surface decoration with Mal-Phe-PEG-20000 caused some auto aggregation of RBCs even in the absence of any antibody. Therefore, in order to examine whether this aggregation can be prevented by minimizing the attachment of Mal-Phe-PEG-20000 chains to RBCs, the RBCs were first PEGylated with Mal-Phe-PEG-5000 in the presence of IT. After removing the excess reagents, the PEGylated RBCs were re-incubated with iminothiolane and Mal-Phe-PEG-20000. This protocol worked very well with type A Rh(D)+ RBCs; no agglutination was observed with anti-A or anti-D antibodies (Table 3). These results were consistent and reproducible. Accordingly, type B Rh(D)+ RBCs were also PEGylated in the same fashion by using a combination of Mal-Phe-PEG-5000 and Mal-Phe-PEG-20000 reagents. Like type A Rh(D)+ cells, these RBCs also exhibited no agglutination at the macroscopic level with anti-B and anti-D antibodies (data not shown).

PEGylation of RBCs with cyanuric chloride-PEG to mask the A and RhD antigens. To compare the efficiency of masking of blood group antigens by modification of RBCs by cyanuric chloride PEG, versus that with thiolation mediated PEGylation, A Rh(D)+ type RBCs were PEGylated with CnCl-PEG-5000. PEGylation with this reagent inhibited the agglutination of the cells with anti-D antibody considerably. However, unlike the modification of RBCs with thiolation mediated PEGylation, optimal masking of RhD antigen was not achieved by this reagent. In contrast, the agglutination of RBCs PEGylated with CnCl-PEG-5000 in the presence of anti-A antibody was comparable to that of cells PEGylated by thiolation mediated PEGylation with the same antibody (Table 3).

Figures 2A, 2B, 2C, 2D, 2E:
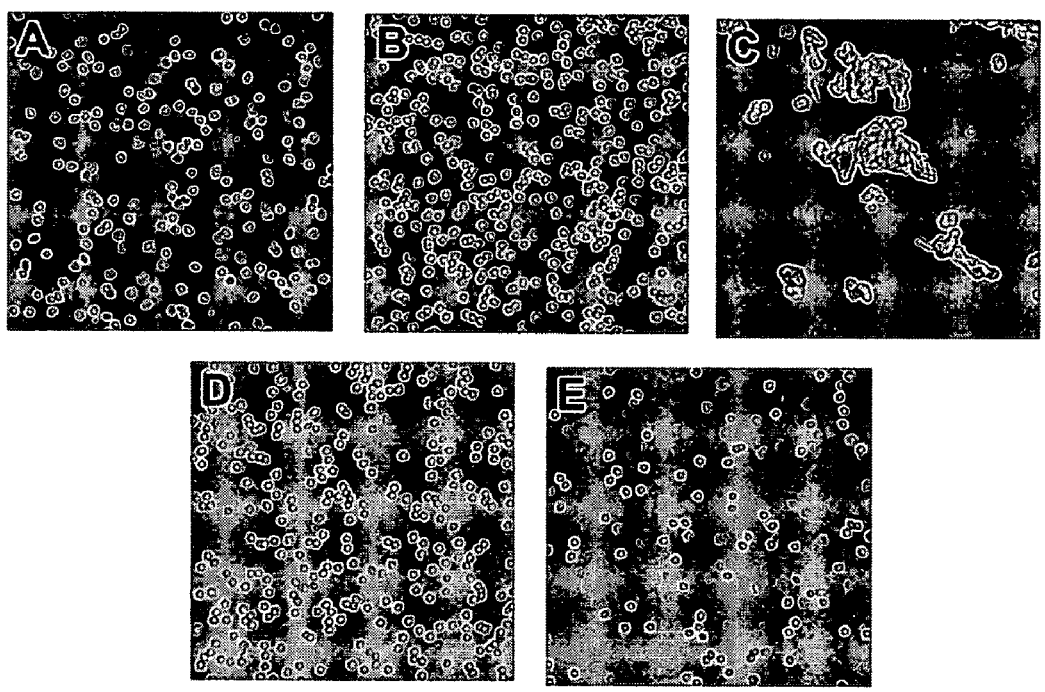
FIG. 2A-2E. Microscopic analysis of PEGylated RBCs of type A Rh(D)+. (A) Unmodified; (B-D) PEGylated in the presence of 2-iminothiolane with (B) Mal-Phe-PEG-5K, (C) Mal-Phe-PEG-20K, (D) Mal-Phe-PEG-5K first and then with Mal-Phe-PEG-20K; and (E) PEGylated with CnCl-PEG-5K alone.

Microscopic evaluation of PEGylated red blood cells in the presence and absence of blood group specific antibodies. PEGylated RBCs were examined under light microscope in the absence of any antibodies to determine if attachment of PEG chains to the membrane of RBCs induces any aggregation of the cells, even though it was not apparent at the macroscopic level. RBCs PEGylated with Mal-Phe-PEG-5000 alone or together with Mal-Phe-PEG-20000 in the presence of IT appeared similar to the RBCs that were not PEGylated (FIGS. 2 B, D and A, respectively). However, RBCs PEGylated with Mal-Phe-PEG-20000 alone contained clumps of aggregates (FIG. 2C), indicating that attachment of only bulky PEG chains (PEG-20000) induced aggregation of RBCs. RBCs PEGylated with CnCl-PEG-5000 also appeared similar to the unmodified RBCs (FIG. 2E).

Figures 3A, 3B, 3C, 3D:
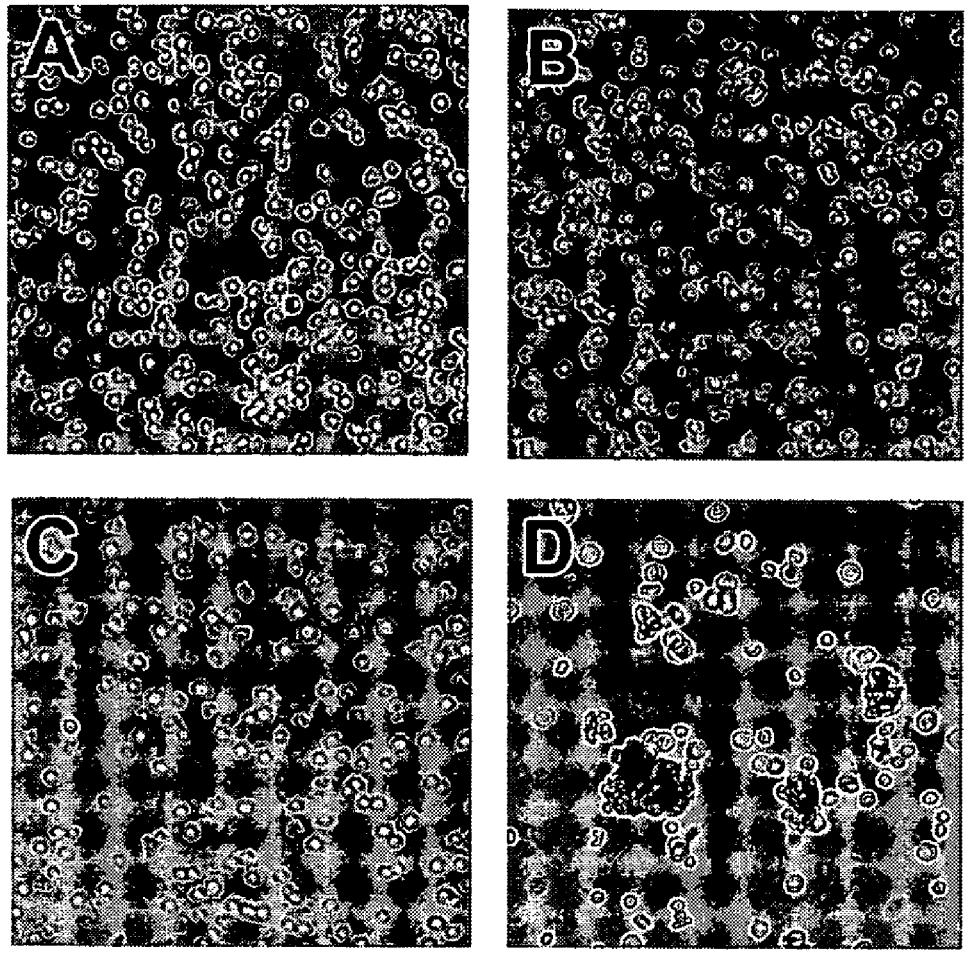
FIG. 3A-3D. Microscopic analysis of PEGylated RBCs in the presence of anti-D antibody. Types (A) A Rh(D)+, (B) B Rh(D)+ and (C) O Rh(D)+ PEGylated by Mal-Phe-PEG-5K in the presence of 2-iminothiolane; (D) Type A Rh(D)+ PEGylated with CnCl-PEG-5K alone.

All the samples (A Rh(D)+, B Rh(D)+ and O Rh(D)+ PEGylated by Mal-Phe-PEG-5000 in the presence of IT) that gave negative results for agglutination with anti-D antibody at the macroscopic level were also examined under the microscope in the presence of the antibody. None of the samples had any clumps of RBCs indicating that PEG-5000 chains attached to the RBCs inhibited the accessibility of RhD antigen to the respective antibody (FIG. 3). Thus all these Rh(D)+ cells behaved as Rh(D)– cells towards anti-D antibody on PEGylation.

RBCs carrying RhCE antigens and PEGylated with Mal-Phe-PEG-5000 in the presence of IT were also subjected to microscopic examination in the presence of anti-C, anti-c, anti-E and anti-e antibodies. RBCs homozygous or heterozygous for Rh C and c or E and e did not exhibit any clumps in the presence of the respective antibodies (data not shown). Thus, thiolation-mediated PEGylation of RBCs with Mal-Phe-PEG-5000 alone can inhibit the agglutination of RBCs in the presence of the most important antigens of Rh system at the microscopic level.

As shown in Table 3, RBCs modified with CnCl-PEG-5000 gave 1+ level of agglutination with anti-D antibody. When these cells were examined under a microscope, clumps of RBCs were detected in the presence of anti-D antibody (FIG. 3D) suggesting that PEGylation with CnCl-PEG-5000 did not endow the RBCs with enough protection against anti-D antibody.

Figures 4A, 4B, 4C, 4D:
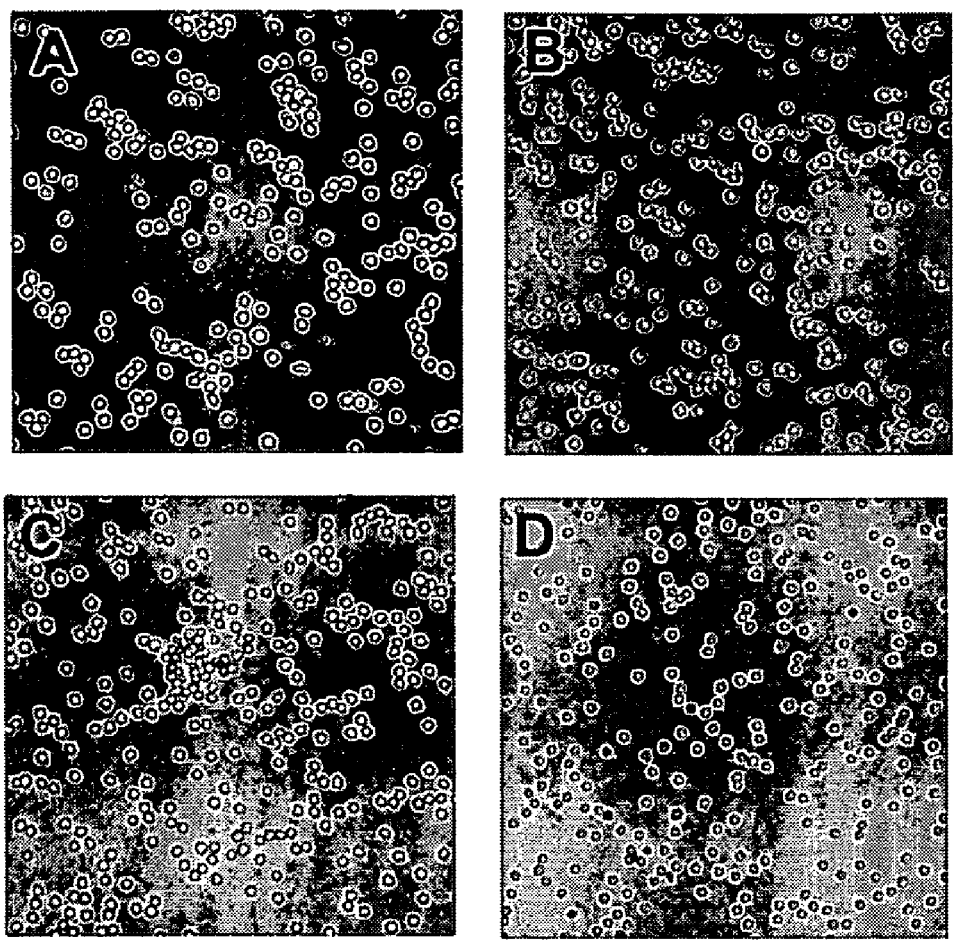
FIG. 4A-4D. Microscopic analysis of RBCs PEGylated with Mal-Phe-PEG-5K first and then with Mal-Phe-PEG-20K in the presence of 2-iminothiolane. Type A Rh(D)+ in the presence of (A) anti-A and (B) anti-D antibodies. Type B Rh(D)+ in the presence of (C) anti-B and (D) anti-D antibodies.

The microscopic evaluation of type A Rh(D)+ RBCs PEGylated with a combination of Mal-Phe-PEG-5000 and Mal-Phe-PEG-20000 detected no clumps in the presence of anti-A and anti-D antibodies (FIGS. 4 A, B), indicating that these antigens were masked by a combination of the two PEG reagents. Type B Rh(D)+ RBCs PEGylated in the same fashion by using a combination of the two PEG reagents exhibited very few small clumps (<1%) in the presence of anti-B antibody under the microscope (FIG. 4C). No such clumps were present in the sample in the presence of anti-D antibody (FIG. 4D).

Figure 5:
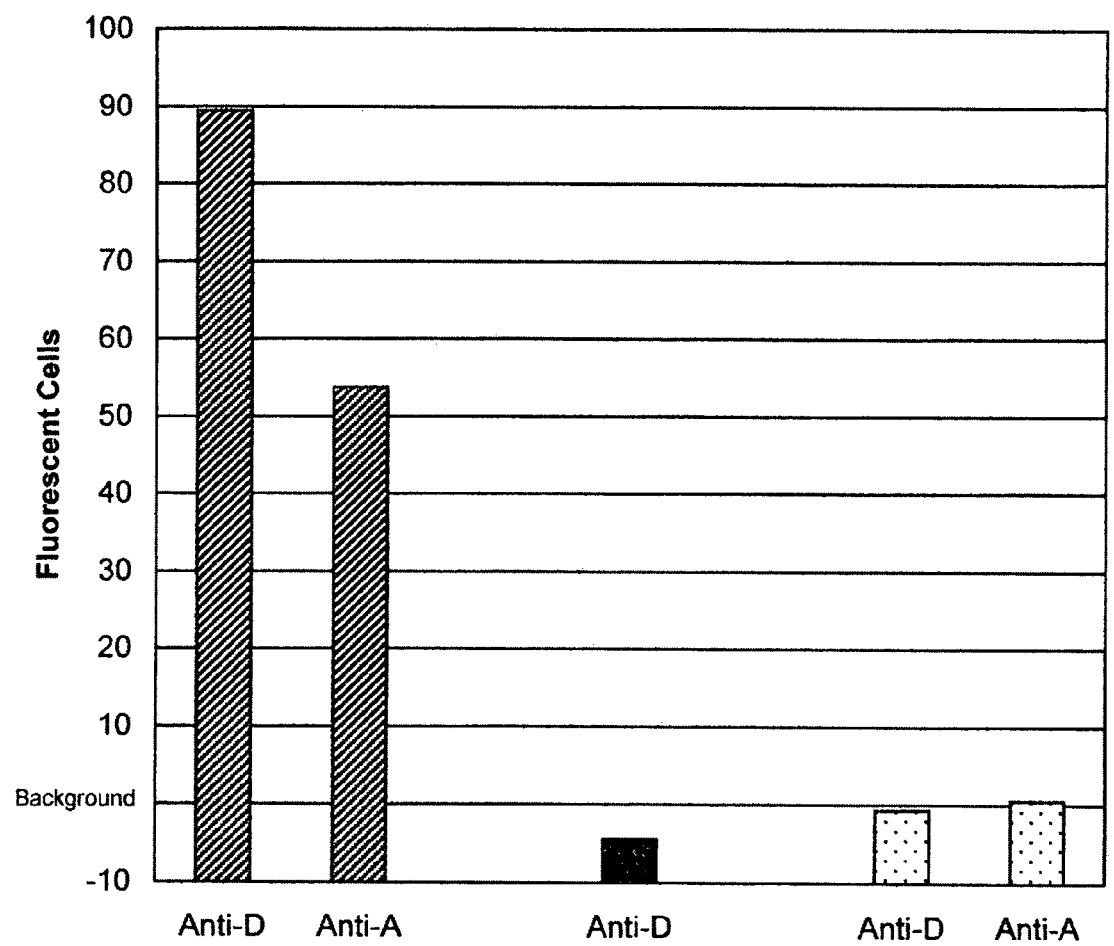
FIG. 5. Flow cytometric analysis of PEGylated RBCs. The binding of anti-A (at 1000× dilution) and anti-D antibodies (at 100× dilution) to RBCs, non-PEGylated (hatched bars) and PEGylated with Mal-Phe-PEG-5000 (filled bars) or with a combination of Mal-Phe-PEG-5000 and Mal-Phe-PEG-20000 (dotted bars).

Flow cytometry of PEGylated cells. The results from flow cytometric analysis of PEGylated cells are presented in FIG. 5. Type A Rh(D)+ RBCs PEGylated with Mal-Phe-PEG-5000 alone were tested for anti-D antibody binding. The percentage of fluorescent cells of this sample was below background, indicating blockage of the D antigen by PEGylation. The same cells PEGylated with Mal-Phe-PEG-5000 and Mal-Phe-PEG-20000 also exhibited similar results for binding anti-D antibody. These doubly modified cells were also tested for anti-A antibody binding. About 1% of these cells were detected to be fluorescent as opposed to 100% labeling of the non-PEGylated cells.

Figures 6A, 6B:
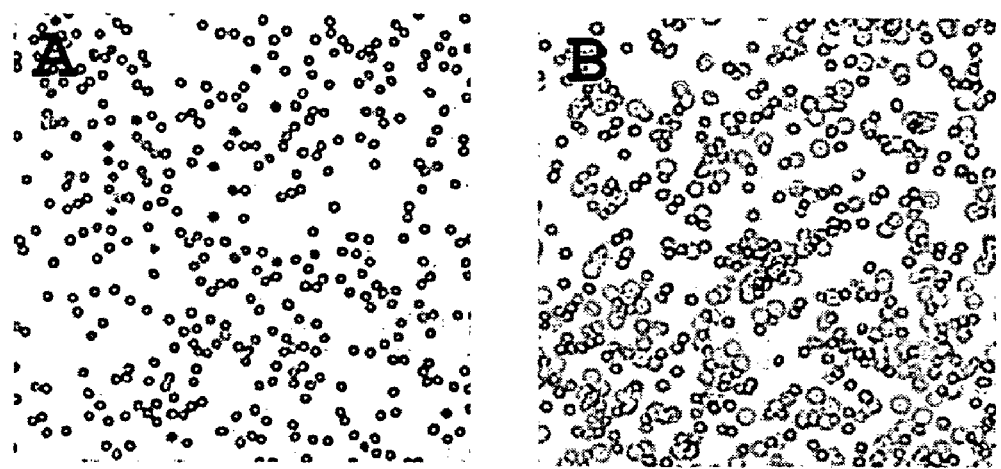
FIG. 6A-6B. Microscopic analysis of PEGylated RBCs in the presence of anti-D antibody. Type A Rh(D)+ RBCs PEGylated by (A) Mal-Phe-PEG-5K after thiolation by DTSSP, (B) SPA-PEG-5K.

Masking of the RhD antigen of RBCs from the respective antibodies by different PEG-5000 chains using thiolation with DTSSP: A Rh (D)+ RBCs PEGylated with Mal-Phe-PEG-5K after thiolation with DTSSP exhibited negative results for agglutination with anti-D antibody, indicating that Mal-Phe-PEG-5K chains could mask RhD antigen sufficiently to prevent agglutination with the respective antibodies at the microscopic level (Table 4, FIG. 6). On the other hand, A Rh(D)+ RBCs PEGylated with SPA-PEG-5K were agglutinated with anti-D antibody although at a much reduced level than control cells. Thus, SPA-PEG-5K chains did not mask RhD antigen as well as Mal-Phe-PEG-5K chains did in thiolation mediated PEGylation. None of these PEG chains could block the agglutination of RBCs with anti-A antibody.

In thiolation mediated PEGylation, an extension arm is added on the side chains of lysine residues of membrane proteins. This extension may have enhanced the accessibility of the bulky PEG reagent, Mal-Phe-PEG-5K. In the active ester PEGylation chemistry, the reagent SPA-PEG-5K directly attacks the side chains of lysine residues. Due to their large size, PEG reagents may be hindered in reaching lysine residues directly. In addition, due to the labile nature of the active ester SPA-PEG-5K may not be able to derivatize enough lysine residues to mask the RhD antigen. Although DTSSP uses active ester chemistry, being a small molecule it could reach the target residues in short time and modify them.

The oxygen delivering capability of the PEGylated cells was measured to determine the influence of PEGylation on the primary function of RBCs. The cells PEGylated with Mal-Phe-PEG-5K after thiolation with DTSSP exhibited slightly enhanced oxygen affinity as compared to the control RBCs (Table 5). However, this enhancement was much lower than the one seen with 2-iminothiolane mediated thiolation (Table 5). Being a small molecule, 2-iminothiolane can cross the membrane and modify hemoglobin altering its oxygen affinity. DTSSP due to its high negative charge is not expected to cross the membrane. However, this reagent may have some impurities that can pass the membrane and influence the oxygen affinity of hemoglobin. PEGylation of RBCs with SPA-PEG-5K did not alter the oxygen affinity of the cells.

Masking of the A antigen of RBCs with a mixture of PEG-reagents: In order to mask A antigen, A Rh(D)+ RBCs PEGylated with Mal-Phe-PEG-5K were subjected to extended thiolation with DTSSP and then PEGylated with Mal-Phe-PEG-20K. RBCs PEGylated with Mal-Phe-PEG-5K were also tested by PEGylation with SPA-PEG-20K for A antigen coverage. The RBCs PEGylated by either Mal-Phe-PEG-20K or by SPA-PEG-20K in the second step were not agglutinated with anti-A or anti-D antibodies (Table 4). No clumps were detected in these samples in the presence of anti-A or anti-D antibodies even under the microscope (FIG. 7) indicating that optimal coverage of the A and D antigens was achieved by PEGylation with both the reagents.

Figures 7A, 7B, 7C, 7D, 7E, 7F, 7G, 7H:
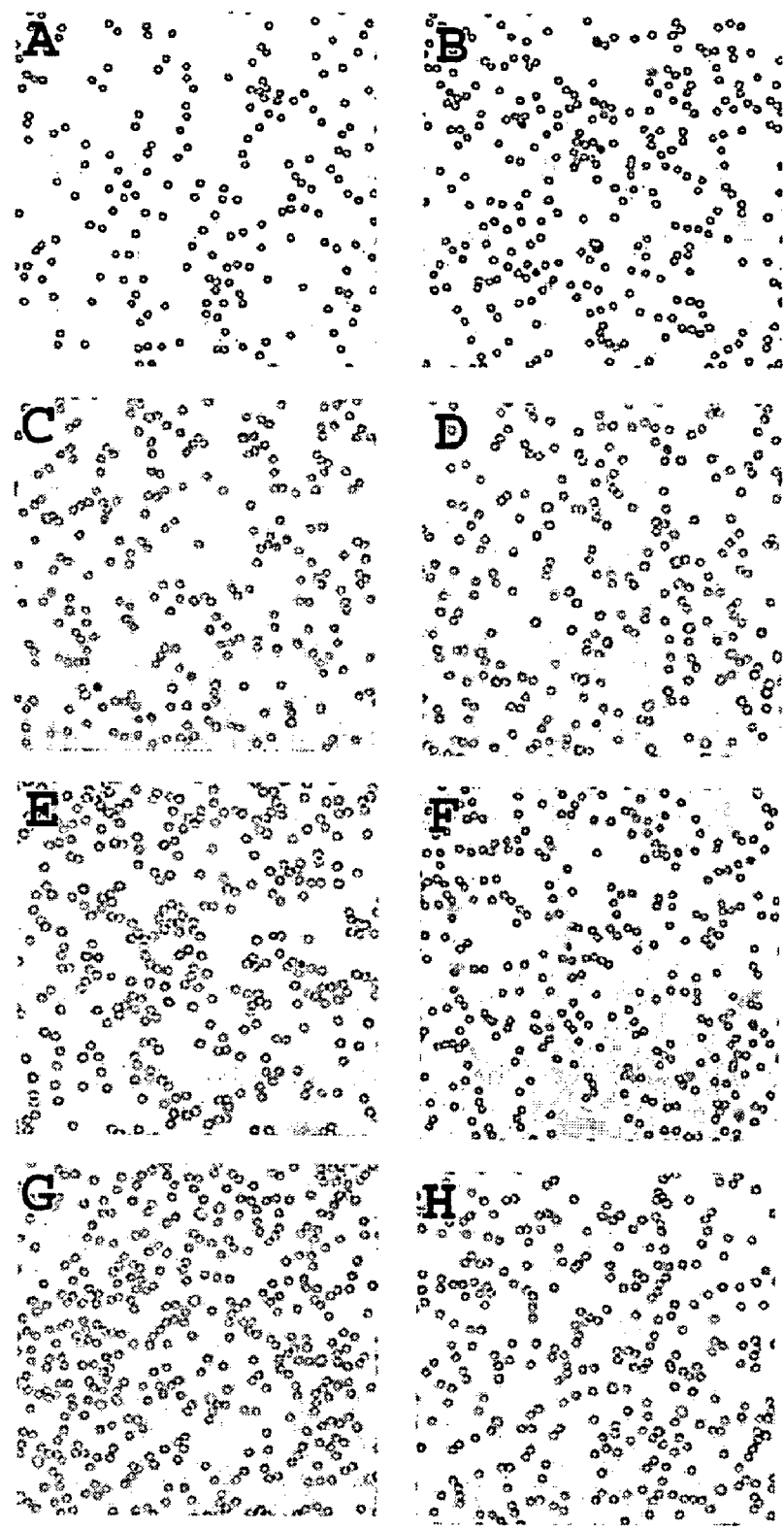
FIG. 7A-7H. Microscopic analysis of PEGylated RBCs in the presence of anti-D (A, C, E and G) and anti-A (B, D, F and H) antibodies. Type A Rh(D)+ RBCs PEGylated by either DTSSP+Mal-Phe-PEG-5K (A, B, C and D) or SPA-PEG-5K (E, F, G and H) in the first step and then by either DTSSP+ Mal-Phe-PEG-20K (A, B, E, and F) or SPA-PEG-20K (C, D, G and H).

A Rh(D)+ RBCs PEGylated with SPA-PEG-5K were also modified with DTSSP mediated PEGylation by Mal-Phe-PEG-20K as well as with SPA-PEG-20K. Both of these samples showed no signs of agglutination with anti-A or anti-D antibody at the macroscopic level (Table 4). However, the cells PEGylated with Mal-Phe-PEG-20K in the second step exhibited very few small clumps (<1%) under the microscope in the presence of anti-A and also anti-D antibody (FIG. 7). On the other hand, the same cells PEGylated by SPA-PEG-20K in the second step did not exhibit any clumps in the presence of anti-A or anti-D antibodies at the microscopic level. These results indicate that optimal PEGylation of the RBCs by smaller PEG chains in the first step is needed to cover A and D antigens in the second step PEGylation by larger PEG chains.

The oxygen affinity of the PEGylated RBCs that used DTSSP mediated thiolation in both the steps increased further as compared to the ones that were modified only once by DTSSP (Table 5). The RBCs that were PEGylated with DTSSP and Mal-Phe-PEG-5K in the first step and with SPA-PEG-20K in the second step exhibited oxygen affinity comparable to that of the precursor cells.

The cells modified by SPA-PEG-5K in the first step and DTSSP mediated PEGylation by Mal-Phe-PEG-20K in the second step also exhibited increased oxygen affinity (Table 7). RBCs PEGylated with SPA-PEG reagents in both the steps exhibited unaltered oxygen affinity as compared to unmodified RBCs.

IV. Discussion

ABO and Rh blood groups are the most important antigens in blood transfusion. ABO mismatched blood transfusion can cause severe transfusion reactions in the recipients and can lead to death. ABO transfusion errors in the United States are reported to cause more noninfectious transfusion deaths every year than any other cause (Sazama, 2003). One in 19,000 RBC units was administered erroneously in New York State alone in the last decade (Linden et al., 2000). At least 47% of the errors involved wrong identification of the patient or the blood. Incorrect interpretation of pre-transfusion bedside compatibility tests has been a major problem in blood transfusion. Trauma conditions do not allow time to do blood typing tests. Allosensitization to other than ABO/RhD antigens is another problem that is encountered in transfusion therapy. All these situations lead to the need of developing universal erythrocytes that can be transfused into a patient without worrying about the blood type.

O Rh– blood group is considered as universal blood in transfusion medicine, especially in emergency conditions. This group blood is at a very high demand at the blood banks all the time. O group RBCs carry H antigen which is a carbohydrate chain with a fucose moiety at the end. A and B antigen specific carbohydrates are added onto H antigen by the blood group specific glycosyltransferases. Therefore, A or B type RBCs can be converted into O type by removing those group specific carbohydrates. Enzymatic approaches have been used to cleave off blood group specific carbohydrate epitopes (Goldstein et al., 1982; Olsson et al., 2004). However, Rh antigens cannot be removed by this method as these antigens are protein based. Thus, it is not possible to generate O Rh– RBCs from other blood types by this technique.

Masking of blood group antigens on RBCs from the respective antibodies by covering the surface of cells with inert polymers is being pursued to develop universal erythrocytes (Bradley et al., 2002; Jeong and Byun, 1996; Scott et al., 1997; U.S. Pat. No. 6,312,685). Unlike the enzymatic approaches that cleave off the blood group specific carbohydrate epitopes, the methodology of covering the cell surface with polymers can mask both the carbohydrate and protein based antigens to prevent the interaction of these antigens with their cognate antibodies.

Various functionalized PEG reagents have been used for the PEGylation of the RBC membrane. However, prior to results presented herein, cyanuric chloride activated PEG had been shown to be the most effective reagent to mask the antigens. Although this PEG reagent has been shown to mask Rh system antigens better than A or B antigens, complete masking of any of these antigens has not been reported (Bradley et al., 2002; Jeong and Byun, 1996; Scott et al., 1997; U.S. Pat. No. 6,312,685).

The results presented herein clearly established that thiolation mediated PEGylation of RBCs generates RBCs with serological behavior comparable to type O Rh(D)– RBCs from types A Rh(D)+, B Rh(D)+ and O Rh(D)+ RBCs. The antigen camouflaging influence of PEGylation of RBCs has been demonstrated by the absence of agglutination of RBCs with the antibodies against ABO and Rh antigens. In addition, examination of the PEGylated RBCs in the presence of antibodies at the microscopic level has confirmed that the A, B, RhCE and RhD antigens are masked to an appropriate level by thiolation mediated PEGylation. This level of inhibition of agglutination with A, B, RhCE and RhD antibodies has not been achieved prior to the present study. Flow cytometric analysis of PEGylated cells also established the same coverage of A and D antigens.

The pattern of surface coverage of RBCs with PEG chains needed to generate universal RBCs does not appear to be simple. The masking of blood group antigens is not a direct correlate of either the total PEG-mass on the cells or the length of the PEG-chains conjugated. A combination of two different size PEG-chains was needed for optimizing the masking of A, B, RhD and RhCE antigens. Modification of the ε-amino groups of Lys residues of the RBC membrane proteins by thiolation, followed by derivatization with either Mal-Phe-PEG-5000 or Mal-Phe-PEG-10000 masked only the RhD antigens from the respective antibodies. But this PEGylation did not mask the group A carbohydrate antigens from their antibodies. On the other hand, PEGylation of RBCs using Mal-Phe-PEG-20000 masked the group A carbohydrate antigens to some degree but did not completely protect the cells from the antibodies to RhD antigens. Similar kind of results have been reported using a PEG-20000 reagent carrying an activated carboxyl group (Mathur et al., 2003). This PEG-20000 reagent could not mask RhD antigens as well as it masked A antigen. These results suggest that the group A antigen epitopes are more exposed to the solvent than the RhD antigens. However, the microscopic examination of the red blood cells PEGylated by Mal-Phe-PEG-20000 showed the presence of some clumping. Thus the masking observed in the agglutination assay of RBCs PEGylated by Mal-Phe-PEG-20000 with anti A antibody may not be a direct correlate of the masking of the A antigen by PEGylation alone. Some of the inhibition of agglutination could be a contribution of the clumping of the cells that can also mask the accessibility of the antigen. The incomplete protection of RBCs PEGylated by Mal-Phe-PEG-20000 from anti-D antibody may also be a consequence of the clumping of these RBC due to PEGylation. Alternatively, it is also conceivable that, due to its large size, Mal-Phe-PEG-20000 is unable to access one or more thiolation modified Lysine residues of RBCs, when used alone, that are accessed by the smaller size Mal-Phe-PEG-5000 to protect the cells from antibodies to Rh antigens. The clumping of the cells due to PEGylation by Mal-Phe-PEG-20000 can be a consequence of interactions between the PEG-20000 chains conjugated to RBCs. The surface coverage of the RBCs with shorter chain Mal-Phe-PEG, i.e. PEG-5000, prior to conjugation with the longer chain PEG apparently reduces the amount of the longer chain Mal-Phe-PEG that can be conjugated to RBCs, thereby reducing the interactions between the PEGylated cells, and hence their clumping together.

The PEG reagents carrying functional groups such as cyanuric chloride and activated carboxyl groups that react directly with the ε-amino groups of the lysine residues of RBCs membrane proteins have been used previously for generating universal red blood cells (Bradley et al., 2002; U.S. Pat. No. 6,312,685). The surface coverage with these reagents is apparently not as efficient as the thiolation mediated maleimide chemistry based PEGylation. It is conceivable that the bulky PEG reagents may not be able to reach the partially exposed lysine residues of the membrane proteins. If PEGylation of one or more of such partially exposed ε-amino groups is essential for thorough masking of the A and B antigens of RBCs, this may not be easily achieved by using the macromolecular PEG-reagents. In thiolation-mediated PEGylation, IT, for example, being a small molecule, can reach the partially buried ε-amino groups of lysine residues and extend the side chain by about 8 Å by introducing 4-mercaptobutyrimidine moiety on the amino group. The sulfhydryl group of the extension arm is now accessible to bulky Mal-Phe-PEG reagents. Thus, sufficient coverage of A and B antigens was achieved with the approach described herein.

The oxygen affinity of RBCs PEGylated using thiolation mediated by iminothiolane is increased about three fold as compared to the unmodified RBC. This may be due to the passage of neutral iminothiolane though the RBC membrane and the concomitant modification of hemoglobin inside RBCs. Accordingly, to overcome this, the thiolation step of the PEGylation protocol was modified to use an anionic, membrane impermeable bifunctional reagent with a disulfide bond in the middle, dithio sulfo succinimidyl propinate (DTSSP) instead of iminothiolane. The membrane protein reacted bifunctional reagent is reduced to membrane protein bound γ-mercapto propylamide chains using triscarboxyethyl phosphine and these are the targets for PEGylation by Mal-Phe-PEG. Even though the chemistry of the linkage of the 'extension arm' to ε-amino groups of membrane proteins are distinct, the latter approach generated another version of universal red blood cells in which carbohydrate and RhD are masked as efficiently as in the version generated using iminothiolane. The oxygen affinity of RBCs did not increase as much as with the iminothiolane mediated PEGylation. In iminothiolane-mediated PEGylation the positive charge on the lysine residues is conserved whereas in DTSSP-mediated PEGylation, the charge is lost. Therefore, the efficient masking of RhD antigen by thiolation-mediated PEGylation in the presence of iminothiolane or DTSSP does not seem to depend on the chemistry of linkage. Rather, it is a consequence of the addition of an extension arm by thiolation. To distinguish between these two structural features, SPA-PEG was used for PEGylation which uses active ester chemistry as DTSSP but without adding an extension arm. SPA-PEG-5K could not mask RhD antigen as efficiently as Mal-Phe-PEG-5K did in thiolation mediated PEGylation, indicating the role of extension arm in thiolation mediated PEGylation. However, a two-step PEGylation using SPA-PEG-5K and SPA-PEG-20K masked the A and RhD antigens as efficiently as the other two thiolation mediated protocols. The PEGylation with SPA-PEG in two steps did not alter the oxygen affinity of the RBCs, making it a preferred approach to make universal red blood cells. Since thiolation mediated PEGylation covers RhD antigen better, a combination of the protocols, where the first step employs the thiolation mediated PEGylation with Mal-Phe-PEG-5K using DTSSP and second step involving PEGylation with SPA-PEG-20K also seems to be a good choice to get optimal coverage of A and RhD antigens and conserve an acceptable level of oxygen affinity.

Optimal masking of RhD antigen on RBCs can be better achieved by using small reagent mediated PEGylation than using PEG reagents that directly attack the amino acid side chains on membrane proteins. However, appropriate reagents need to be used to avoid passage of the RBC membrane. Two-iminothiolane or DTSSP thiolation mediated PEGylation helped masking the RhD antigen in one step PEGylation by Mal-Phe-PEG-5K. DTSSP altered the oxygen affinity of RBCs less than 2-iminothiolane. PEGylation with SPA-PEG-20K in the second step not only attained appropriate masking of A antigen but also maintained the oxygen affinity of the cells to a reasonable extent. Therefore, DTSSP mediated PEGylation by Mal-Phe-PEG-5K may be used to cover RhD antigen alone and an additional step of PEGylations by SPA-PEG-20K may be added in the second step to mask A or B antigens.

All the types of RBCs that were PEGylated using iminothiolane-mediated chemistry were demonstrated to have ABO/RhD antigens masked completely from the antibodies. It is possible that blood cell antigens other than ABO/RhD antigens are also masked by these PEG chains and can escape from being detected by their respective antibodies. In such case these RBCs can prevent the development of alloimmunization in patients even after repeated transfusions.

All publications mentioned herein are hereby incorporated in their entirety into the subject application. While the foregoing invention has been described in some detail for purposes of clarity and understanding, it will be appreciated by one skilled in the art, from a reading of the disclosure, that various changes in form and detail can be made without departing from the true scope of the invention set forth in the appended claims.

REFERENCES

Avent N D and Reid M E. The Rh blood group system: a review. Blood. 95:375-387, 2000.

Blackall D P, Armstrong J K, Meiselman H J, Fisher T C. Polyethylene glycol-coated red blood cells fail to bind glycophorin A-specific antibodies and are impervious to invasion by the Plasmodium falciparum malaria parasite. Blood. 97:551-556, 2001.

Bradley A J, Murad K L, Regan K L, Scott M D. Biophysical consequences of linker chemistry and polymer size on stealth erythrocytes: size does matter. Biochim Biophys Acta. 1561:147-158, 2002.

Bradley A J, Test S T, Murad K L, Mitsuyoshi J, Scott M D. Interactions of IgM ABO antibodies and complement with methoxy-PEG-modified human RBCs. Transfusion. 41:1225-1233, 2001.

Castro O, Sandler S G, Houston-Yu P, Rana S. Predicting the effect of transfusing only phenotype-matched RBCs to patients with sickle cell disease: theoretical and practical implications. Transfusion. 42: 684-690, 2002.

Fisher T C, Armstrong J K. Red blood cells covalently bound with two different polyethylene glycol derivatives. U.S. Pat. No. 6,312,685, issued Nov. 6, 2001.

Goldstein J, Siviglia G, Hurst R, Lenny L, Reich L. Group B erythrocytes enzymatically converted to group O survive normally in A, B, and O individuals. Science. 215:168-170, 1982.

de Isla N G, Riquelme B D, Rasia R J, Valverde J R, Stoltz J F. Quantification of glycophorin A and glycophorin B on normal human RBCs by flow cytometry. Transfusion. 43: 1145-1152, 2003.

Issitt P D. Race-related red cell alloantibody problems. Br J Biomed Sci. 51: 158-167, 1994.

Jeong S T, Byun S M. Decreased agglutination of methoxy-polyethylene glycol attached red blood cells: significance as a blood substitute. Art Cells Blood Subs and Immob Biotech. 24: 503-511, 1996.

Lenny L L, Hurst R, Goldstein J, Galbraith R A. Transfusions to group O subjects of 2 units of red cells enzymatically converted from group B to group O. Transfusion. 34: 209-214, 1994.

Lenny L L, Hurst R, Zhu A, Goldstein J, Galbraith R A. Multiple-unit and second transfusions of red cells enzymatically converted from group B to group O: report on the end of phase 1 trials. Transfusion. 35:899-902, 1995.

Linden J V, Wagner K, Voytovich A E, Sheehan J. Transfusion errors in New York State: an analysis of 10 years' experience. Transfusion. 40(10):1207-13, 2000.

Manjula B N, Tsai A, Upadhya R, et al. Site-specific PEGylation of hemoglobin at Cys-93(beta): correlation between the colligative properties of the PEGylated protein and the length of the conjugated PEG chain. Bioconjug Chem. 14:464-472, 2003.

Mathur S, Clark B, Castro G, Zhou X M, Bowers S, Stassinopoulos A. Efficient full unit PEGylation of human red blood cells (RBC) using linear methoxy-capped polyethylene glycol (mPEG). Blood. 102: 556A, 2003.

Olsson M L, Hill C A, de la Vega H, et al. Universal red blood cells—enzymatic conversion of blood group A and B antigens. Transfus Clin Biol. 11:33-39, 2004.

Roberts M J, Bentley M D, Harris J M. Chemistry for peptide and protein PEGylation. Advanced Drug Delivery reviews. 54:459-476, 2002.

Sabolovic D, Sestier C, Perrotin P, Guillet R, Tefit M, Boynard M. Covalent binding of polyethylene glycol to the surface of red blood cells as detected and followed up by cell electrophoresis and rheological methods. Electrophoresis. 21:301-306, 2000.

Sazama, K. Transfusion errors: scope of the problem, consequences, and solutions. Curr Hematol Rep. 2(6):518-21, 2003.

Scott M D, Murad K L, Koumpouras F, Talbot M, Eaton J W. Chemical camouflage of antigenic determinants: Stealth erythrocytes. Proc Natl Acad Sci USA. 94:7566-7571, 1997.

TABLE 1

Agglutination assay of PEGylated RBCs to evaluate the masking of A and D antigens.

| RBC Type | Modifying Reagents | Anti-A | Anti-B | Anti-D |
|---|---|---|---|---|
| A Rh(D)+ | None | 4+ | NA | 3+ |
|  | Mal-Phe-PEG-5K | 4+ | NA | 3+ |
|  | IT + Mal-Phe-PEG-5K | 4+ | NA | 0 |
| B Rh(D)+ | None | NA | 4+ | 3+ |
|  | IT + Mal-Phe-PEG-5K | NA | 4+ | 0 |
| O Rh(D)+ | None | NA | NA | 3+ |
|  | IT + Mal-Phe-PEG-5K | NA | NA | 0 |

NA = Not applicable

TABLE 2

Agglutination assay of PEGylated RBCs to evaluate the masking of RhCE antigens

| RBC Phenotype | Modifying Reagents | Anti-C | Anti-c | Anti-E | Anti-e |
|---|---|---|---|---|---|
| DCcEe | None | 3+ | 3+ | 3+ | 3+ |
|  | IT + Mal-Phe-PEG-5K | 0 | 0 | 0 | 0 |
| DCe (R1R1) | None | 3+ | NA | NA | 3+ |
|  | IT + Mal-Phe-PEG-5K | 0 | NA | NA | 0 |
| DcE (R2R2) | None | NA | 3+ | 3+ | NA |
|  | IT + Mal-Phe-PEG-5K | NA | 0 | 0 | NA |

NA = Not applicable

TABLE 3

Influence of PEG chain combinations on masking A and RhD antigens of PEGylated RBCs

| Modifying PEG Reagent* | Anti-A | Anti-D |
|---|---|---|
| None | 4+ | 3+ |
| Mal-Phe-PEG-5K | 4+ | 0 |
| Mal-Phe-PEG-10K | 2+ | 0 |
| Mal-Phe-PEG-20K | 1+ | 1+ |
| Mal-Phe-PEG-5K + 10K† | 4+ | 0 |
| Mal-Phe-PEG-5K + 20K† | 1+ | 1+ |
| Mal-Phe-PEG-5K + 10K + 20K† | 3+ | 0 |
| Mal-Phe-PEG-5K &20K‡ | 0 | 0 |
| CnCl-PEG-5K | 4+ | 1+ |

*All the incubations were carried out in the presence of IT.
†The PEG reagents of different chain lengths were present together in the reaction mixture.
‡The RBCs were first PEGylated with Mal-Phe PEG-5K. After removing the excess reagents by washing, the PEGylated RBCs were reincubated with Mal-Phe-PEG-20K in the presence of IT.

TABLE 4

Agglutination assay of PEGylated RBCs to evaluate the masking of the A and D antigens

| Modifying Reagents | | Agglutination With | |
|---|---|---|---|
| Step 1 | Step 2 | Anti-A | Anti-D |
| None | None | 4+ | 3+ |
| DTSSP + Mal-Phe-PEG-5K | None | 4+ | 0 |

TABLE 4-continued

Agglutination assay of PEGylated RBCs to evaluate the masking of the A and D antigens

| Modifying Reagents | | Agglutination With | |
|---|---|---|---|
| Step 1 | Step 2 | Anti-A | Anti-D |
| SPA-PEG-5K | None | 4+ | 1+ |
| DTSSP + Mal-Phe-PEG-5K | DTSSP + Mal-Phe-PEG-20K | 0 | 0 |
| DTSSP + Mal-Phe-PEG-5K | SPA-PEG-20K | 0 | 0 |
| SPA-PEG-5K | DTSSP + Mal-Phe-PEG-20K | 0 | 0 |
| SPA-PEG-5K | SPA-PEG-20K | 0 | 0 |

TABLE 5

Oxygen affinity of the PEGylated RBCs

| Modifying Reagents | | |
|---|---|---|
| Step 1 | Step 2 | P50 |
| None | None | 27.5 |
| DTSSP + TCEP + Mal-Phe-PEG-5K | None | 24.0 |
| SPA-PEG-5K | None | 27.5 |
| DTSSP + TCEP + Mal-Phe-PEG-5K | DTSSP + TCEP + Mal-Phe-PEG-20K | 12.0 |
| DTSSP + TCEP + Mal-Phe-PEG-5K | SPA-PEG-20K | 22.5 |
| SPA-PEG-5K | DTSSP + TCEP + Mal-Phe-PEG-20K | 15.0 |
| SPA-PEG-5K | SPA-PEG-20K | 27.5 |
| IT + Mal-Phe-PEG-5K | None | 9.0 |
| IT + Mal-Phe-PEG-5K | IT + Mal-Phe-PEG-20K | 8.2 |

What is claimed is:

1. A method of preparing pegylated red blood cells comprising a polyethylene glycol (PEG) having a molecular weight of 5 K daltons and a polyethylene glycol (PEG) having a molecular weight of 20 K daltons, the method comprising the sequential steps of:
    (a) introducing a polyethylene glycol (PEG) having a molecular weight of 5 K daltons onto the red blood cells to prepare pegylated red blood cells comprising a polyethylene glycol (PEG) having a molecular weight of 5 K daltons, wherein either (1) the red blood cells are contacted with a chemical thiolating compound that produces a thiolated amino group on a membrane protein of the red blood cells and the polyethylene glycol (PEG) is attached to the thiolated amino group via a maleimide or (2) the polyethylene glycol (PEG) is a succinimidyl-propionate-activated (SPA)-polyethylene glycol (PEG);
    (b) removing excess reagents; and
    (c) introducing a polyethylene glycol (PEG) having a molecular weight of 20 K daltons onto the pegylated red blood cells comprising the polyethylene glycol (PEG) having a molecular weight of 5 K daltons to prepare pegylated red blood cells comprising a polyethylene glycol (PEG) having a molecular weight of 5 K daltons and a polyethylene glycol (PEG) having a molecular weight of 20 K daltons, wherein either (1) the red blood cells are contacted with a chemical thiolating compound that produces a thiolated amino group on a membrane protein of the red blood cells and the polyethylene glycol (PEG) is attached to the thiolated amino group via a maleimide or (2) the polyethylene glycol (PEG) is a succinimidyl-propionate-activated (SPA)-polyethylene glycol (PEG);
    wherein the polyethylene glycol (PEG) is a methoxy PEG; and
    wherein pegylation of the red blood cells masks a Rh antigen and one or more of A antigen and B antigen.

2. The method of claim 1, wherein step (a) comprises contacting the red blood cells with a chemical thiolating compound that produces a thiolated amino group on a membrane protein of the red blood cells and wherein the polyethylene glycol (PEG) is attached to the thiolated amino group via a maleimide.

3. The method of claim 2, wherein the chemical thiolating compound is iminothiolane.

4. The method of claim 2, wherein the chemical thiolating compound is dithio sulfo succinimidyl propinate (DTSSP).

5. The method of claim 1, wherein in step (a), the polyethylene glycol (PEG) is a succinimidyl-propionate-activated (SPA)-polyethylene glycol (PEG).

6. The method of claim 1, wherein step (c) comprises contacting the red blood cells with a chemical thiolating compound that produces a thiolated amino group on a membrane protein of the red blood cell and wherein the polyethylene glycol (PEG) is attached to the thiolated amino group via a maleimide.

7. The method of claim 6, wherein the chemical thiolating compound is iminothiolane.

8. The method of claim 6, wherein the chemical thiolating compound is dithio sulfo succinimidyl propinate (DTSSP).

9. The method of claim 1 wherein in step (c), the polyethylene glycol (PEG) is a succinimidyl-propionate-activated (SPA)-polyethylene glycol (PEG).

10. The method of claim 1, wherein the polyethylene glycol (PEG) in step (a) is a maleimide methoxypolyethylene glycol.

11. The method of claim 10, wherein the maleimide methoxypolyethylene glycol is a maleimide phenyl methoxypolyethylene glycol.

12. The method of claim 10, wherein the maleimide methoxypolyethylene glycol is a maleimidophenyl carbamate of methoxypolyethylene glycol.

13. The method of claim 1, wherein the polyethylene glycol (PEG) in step (a) is a maleimide methoxypolyethylene glycol and wherein the polyethylene glycol (PEG) in step Cc) is a succinimidyl-propionate-activated (SPA)-polyethylene glycol (PEG).

14. The method of claim 1, wherein the Rh antigen is one or more of Rh(D), Rh(C), Rh(c), Rh(E) and Rh(e).

15. The method of claim 1, wherein pegylation of the red blood cells does not alter the oxygen affinity of the red blood cells by more than 20%.

16. The method of claim 1, wherein pegylation of the red blood cells does not alter the oxygen affinity of the red blood cells by more than 15%.

17. The method of claim 1, wherein the method is carried out at a temperature between about room temperature and about 4° C.

18. The method of claim 1, wherein the method is carried out at a pH of about pH 7.4-9.2.

19. The method of claim 1, wherein the method is carried out for about 2 hours.

20. A pegylated red blood cell comprising a polyethylene glycol (PEG) having a molecular weight of 5 K daltons and a polyethylene glycol (PEG) having a molecular weight of 20 K daltons produced by the method of claim 1.

21. A composition comprising the pegylated red blood cell of claim 20 and a pharmaceutically acceptable carrier.

* * * * *